United States Patent [19]
Johansson

[11] Patent Number: 5,855,573
[45] Date of Patent: Jan. 5, 1999

[54] SANITARY PANTY

[75] Inventor: Kerstin Johansson, Ulricehamn, Sweden

[73] Assignee: Mölnlycke AB, Göteborg, Sweden

[21] Appl. No.: 841,331

[22] Filed: Apr. 30, 1997

Related U.S. Application Data

[63] Continuation of Ser. No. 617,778, filed as PCT/SE94/00932, Oct. 4, 1994, abandoned.

[30] Foreign Application Priority Data

Oct. 7, 1993 [SE] Sweden .................................. 9303283

[51] Int. Cl.$^6$ ............................... A61F 13/15; A49B 9/00
[52] U.S. Cl. ...................... 604/385.2; 604/395; 604/396; 2/401
[58] Field of Search .................................. 604/385.1–402; 2/71–73, 76, 78.3, 109–112, 212–213, 220–221, 229, 236–237, 311–312, 400–404

[56] References Cited

U.S. PATENT DOCUMENTS

| | | |
|---|---|---|
| 4,430,086 | 2/1984 | Repke . |
| 4,585,447 | 4/1986 | Karami .................. 604/385.2 |
| 4,897,084 | 1/1990 | Ternstrom et al. ................... 604/385.2 |
| 4,935,021 | 6/1990 | Huffman et al. ...................... 604/385.2 |
| 5,411,498 | 5/1995 | Fahrenkrug et al. ................ 604/385.2 |
| 5,415,644 | 5/1995 | Enloe .................................... 604/385.2 |

FOREIGN PATENT DOCUMENTS

| | | |
|---|---|---|
| 188667 | 2/1957 | Austria . |
| 0 033 569 | 8/1981 | European Pat. Off. . |
| 0 073 183 | 3/1983 | European Pat. Off. . |
| 37 40 002 | 6/1988 | Germany . |
| 434006 | 7/1984 | Sweden . |
| 902691 | 8/1962 | United Kingdom . |
| 1356465 | 6/1974 | United Kingdom . |
| 2 183 449 | 6/1987 | United Kingdom . |
| 90/09159 | 8/1990 | WIPO . |

OTHER PUBLICATIONS

Translation of 188,667, 5 pages.

Primary Examiner—Aaron J. Lewis
Assistant Examiner—K. M. Reichle
Attorney, Agent, or Firm—Burns, Doane, Swecker & Mathis, L.L.P.

[57] ABSTRACT

The present invention relates to a sanitary panty including a back-part (2), a front-part (1), an intermediate crotch-part (3) and elastic devices (11–14) which extend between the front-part and the back-part of the panty and function to press an absorbent body (8) permanently mounted or removably attached to the panty into abutment with the wearer's body. Two elastic devices (11, 12) extend from a region (V) in the crotch-part of the panty to the front-edge of the front-part (1) while diverging relative to one another and extending generally symmetrically in relation to a central line (A—A) which extends through the back-part (2), the crotch-part (3) and the front-part (1) of the panty.

28 Claims, 4 Drawing Sheets

5,855,573

SANITARY PANTY

This application is a continuation of application Ser. No. 08/617,778, filed as PCT/SE94/00932 Oct. 4, 1994, now abandoned.

FIELD OF THE INVENTION

The present invention relates to a sanitary panty or to a light-incontinence guard having a back-part, a front-part, an intermediate crotch-part and elastic devices which extend between the front-part and the back-part of the panty and which function to press an absorbent body permanently mounted or removably attached to the panty into abutment with the wearer's body.

DISCUSSION OF RELATED ART

SE-B-434,006 describes a sanitary panty of this kind which includes a plurality of mutually parallel elastic threads which extend in a straight line between the front and back parts of the panty. The object of the panty according to this publication is to eliminate the drawbacks of sanitary panties that are produced entirely of elastic material, by causing the uniformly distributed elastic threads to press a sanitary napkin or like article carried in the panty into essentially uniform abutment with the wearer's body. However, the known panty has not been found to provide a completely satisfactory solution to the problem of providing a sanitary panty which is comfortable to wear and which prevents leakage from an absorbent body or pad carried by the panty.

OBJECTS AND SUMMARY

An object of the present invention is to solve this problem more effectively than known sanitary panties and to provide a sanitary panty which is comfortable to wear and which is highly effective in preventing leakage from an absorbent body carried by the panty.

This object is achieved in accordance with the invention by means of a sanitary panty of the kind defined in the introduction which is characterized in that two elastic devices extend from a region in the crotch-part of the panty to the front-edge of the front-part of the panty while diverging in relation to one another and extending generally symmetrically in relation to a center line through the back-part, the crotch-part and the front-part of the panty. In addition to pressing corresponding parts of the absorbent body into abutment with the wearer's body within the region in which the elastic devices extend, the elastic devices also form the absorbent body into a shape which conforms with the anatomy of the wearer, wherein those parts of the absorbent body which lie between neighbouring elastic devices will also conform well to the wearer's anatomy.

According to one preferred embodiment of the inventive panty, at least one elastic device extends from a region which is located in the crotch region of the wearer to the rear-edge of the back-part of the panty essentially along i.e., parallel and adjacent to, a central line which extends through the front-part, the crotch-part and the back-part of the panty. Preferably, further elastic devices extend divergently relative to one another and symmetrically in relation to a central line passing through the front-part, the crotch-part and the back-part of the panty, from the center-part of said crotch-part to the rear-edge of the back-part and to the front-edge of said front-part. The outermost elastic devices of said further elastic devices in relation to said central line extend along the side-edges of an absorbent body that coacts with the panty, at least within the center-part of the crotch-part. The elastic devices may conveniently comprise elastic threads, ribbons or bands and the panty may be comprised of two layers or sheets with the elastic devices mounted therebetween. The aforesaid two sheets are preferably joined together and to the elastic devices by gluing or ultrasonic welding.

BRIEF DESCRIPTION OF THE DRAWINGS

Exemplifying embodiments of an inventive sanitary panty will now be described with reference to the accompanying drawings, in which.

DETAILED DESCRIPTION OF PREFERRED EMBODIMENTS

Figure 1:
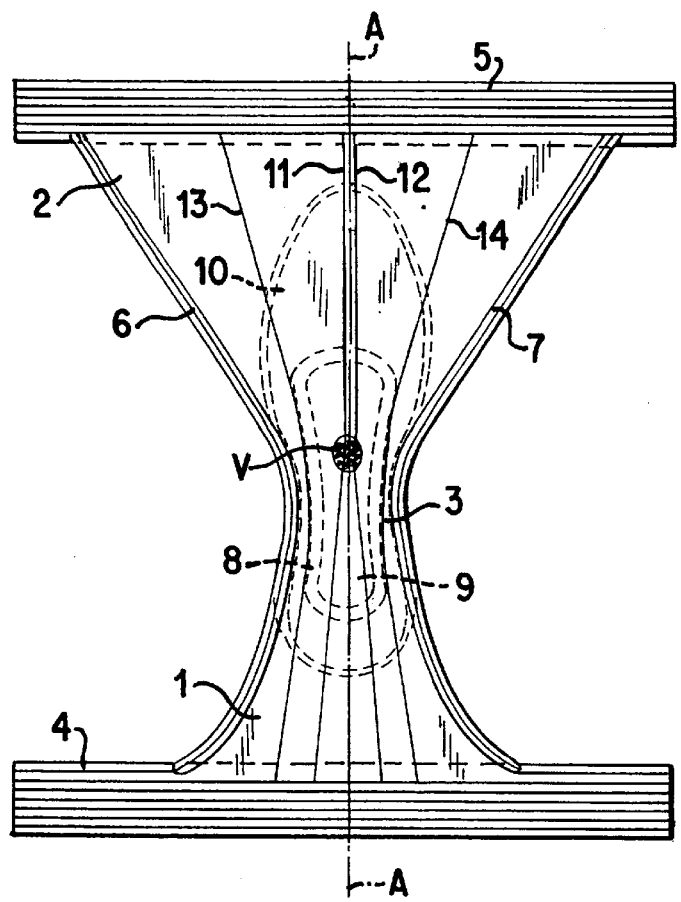
FIG. 1 is a view of a first embodiment of an inventive sanitary panty taken from above, before fastening the waist-parts of the panty together.

FIG. 1 illustrates a sanitary panty according to one embodiment of the invention and shows the panty in a stage of manufacture prior to joining together the front and the rear waist-parts. The illustrated panty includes a front-part 1, a back-part 2 and an intermediate crotch-part 3. The panty is also provided conventionally with a waist elastic, which in the illustrated case has the form of an elastic ribbon 4, 5 mounted along the front-part and the back-part of the waist edge, and a leg elastic in the form of elastic threads 6, 7 extending along the side-contours of the panty between the elastic ribbons 4, 5. In the illustrated case, two elastic threads are mounted along each side-edge of the panty, although it will be understood that the leg elastic may, instead, consist of more or fewer threads than shown or of elastic ribbons or the like. FIG. 1 also shows an absorbent body or pad 8 in broken lines, which may be either attached firmly to the panty or removably joined thereto. The illustrated absorbent body 8 is comprised of a primary absorbent body 9 and a secondary absorbent body 10 and is particularly suited for night use.

The panty is also provided with two elastic threads 11, 12 which extend between the respective elastic ribbons 4 and 5 of the front and back parts 1, 2, symmetrically in relation to a center line A—A extending in the longitudinal direction of the panty. The threads 11, 12 extend close together and parallel with the longitudinal panty line, from the waist-edge of the back-part 2 or the rear-edge of said back-part to a crotch region V, which when the panty is worn is located in the crotch region of the wearer. The threads 11, 12 extend divergently from this region V to the waist-edge or the front-edge of the front-part of the panty.

Figure 4:
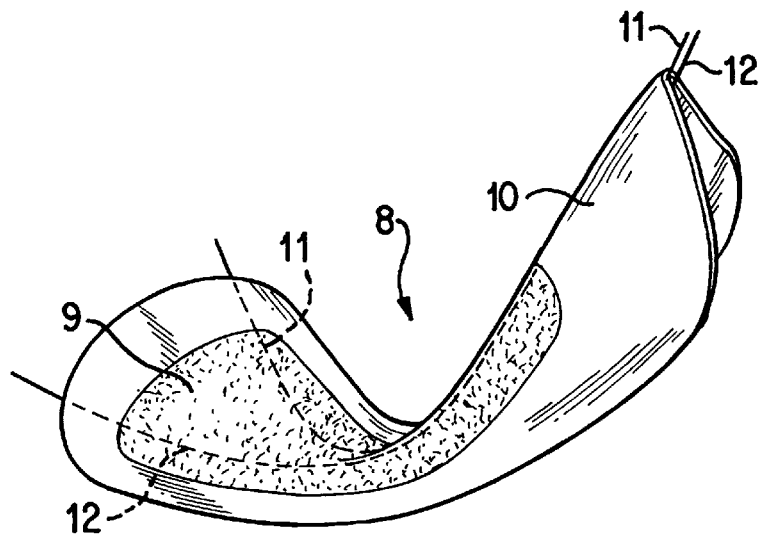
FIG. 4 is a schematic illustration showing deformation of an absorbent body inserted in a panty worn by a user.

When wearing a panty constructed in accordance with the FIG. 1 embodiment, those parts of the threads 11, 12 which diverge forwardly from the region V strive to bring the absorbent body 8 to a basin-like shape within this region, this basin-like shape corresponding well to the wearer's anatomy within this region. Those mutually parallel parts of the threads 11, 12 which extend rearwardly from the region V strive to press corresponding central parts of the absorbent body 8 in between the wearer's buttocks when the panty is worn, thereby causing the absorbent body to lie safely against the wearer's body, at least within the crotch-part and the beginning of the back-part of the panty, so as to provide effective safety against rearward leakage. The aforementioned shaping of the absorbent body is illustrated schematically in FIG. 4.

The panty illustrated in FIG. 1 also includes elastic threads 13, 14 which lie laterally outside the threads 11, 12 and which are mutually convergent in the front part of the panty and are mutually divergent in the back part of the panty. The elastic threads 13, 14 follow the side contours of the primary absorbent body 9, along a major part of their length extension. The threads 13, 14 thus ensure that the side-edges of the primary absorbent body will be pressed into sealing abutment with the wearer's body and also contribute towards ensuring that the secondary absorbent body will follow the wearer's body effectively. It should be mentioned in this connection that the secondary absorbent body is thin and very pliable and is intended to form an additional safety zone for absorbing any leakage that may occur during long-term use of the absorbent body, for instance over a full night, and that its absorption capacity may be relatively small.

When the absorbent body that coacts with the sanitary panty is to form an integral part of the pantie, the absorbent body is preferably anchored to the panty in the stage of manufacture illustrated in FIG. 1, in which the aforedescribed elastic elements are in a stretched state. When manufacture of the panty is completed, the elastic elements strive to contract to a relaxed or tensionless state. This results in the formation of folds in those regions of the panty which lie outside the primary absorbent body 9, and the threads will contract to a generally relaxed state within these regions. Within the region of the primary absorbent body 9, the absorbent body counteracts gathering of the panty into folds, to a greater or lesser extent dependent on the stiffness thereof. Present-day thin absorbent bodies are extremely pliable and will therefore be folded by the elastic threads, although the threads are prevented from relaxing totally. Thus, when the panty is put on the wearer's body, the folds in the absorbent body 9 will be smoothed out and the body will be brought into abutment with the wearer's body by the elastic force in respective threads 11–14. The absorbent body 9 will obtain a concave basin-like shape from the region V forwards, due to the wearer's anatomy, causing the contracting force exerted by the threads 11–14 within this region to strive to retain this basin-like shape while, at the same time, those parts of the absorbent body 9 which lie along the threads will be pressed into sealing abutment with the wearer's body. The mutually parallel parts of the threads 11, 12 ensure that the part of the absorbent body 9 that lies rearwards of the region V will be deformed so as to conform to the shape of the wearer's anatomy in this region and so that the part of the absorbent body that lies between the wearer's buttocks will come into sealing abutment with the wearer's body. In addition to ensuring that the side-edges of the absorbent body 9 will sealingly abut the wearer's body, the elastic threads 13, 14 also function to prevent the formation of folds or buckles in the panty or in the secondary absorbent body.

When the panty illustrated in FIG. 1 is intended to be used together with a removable absorbent body, the absorbent body should be inserted with the elastic threads outwardly stretched at least within the region of attachment of the primary absorbent body. A panty of this kind will function essentially in the manner described above with reference to an integrated absorbent body. This is also a natural method of attaching the absorbent body, since folds would otherwise form in the crotch-part of the panty. It should be mentioned in this connection that a removable absorbent body which is intended to coact with the inventive panty will preferably have a stiffness such as not to be folded by the elastic threads after attachment to the panty, but merely curved.

Figure 2:
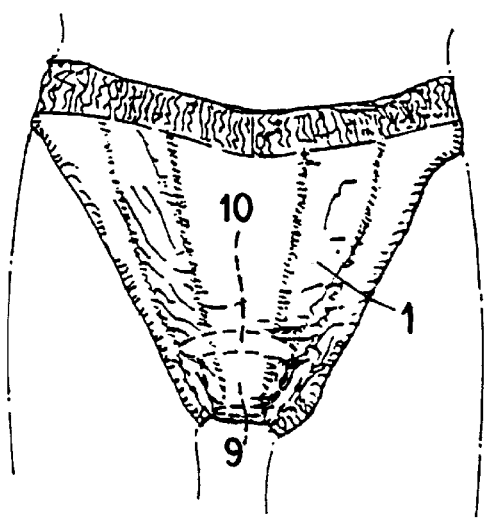
FIGS. 2 and 3 are front and rear views respectively showing the sanitary panty of FIG. 1 when assembled and when worn.
Figure 3:
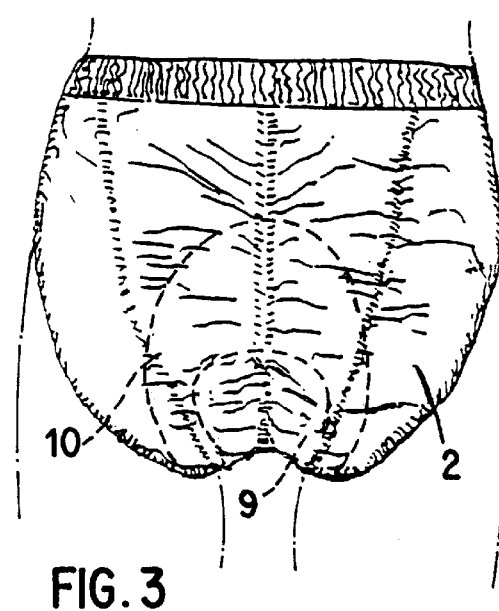

FIGS. 2 and 3 illustrate schematically the form taken by the sanitary panty of FIG. 1 when worn, the relevant parts of the wearer's body being shown in broken lines.

Figure 7:
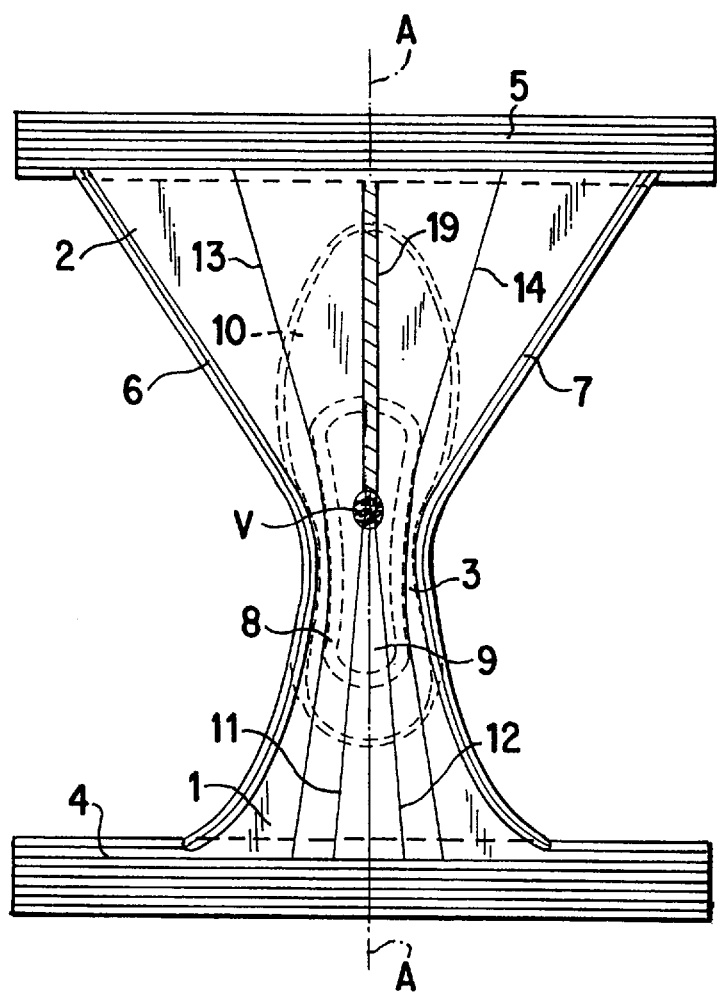
FIG. 7 is a view similar to FIG. 1 illustrating a further embodiment of an inventive sanitary panty.

In the case of the FIG. 1 embodiment, the elastic devices 11–14 are elastic threads. It will be understood, however, that the necessary elasticity of the panty can be achieved in ways other than with the aid of elastic threads. For instance, the elastic devices may have the form of elastic bands, ribbons or elastic film, or nonwoven material cut to the desired shape. It is also conceivable to produce the panty from an elastic material and to remove the elastic properties of the material in some suitable way within desired regions or areas. Different types of elastic material may be combined in the illustrated panty. For instance, soft bands or ribbons of elastic foam may be used as leg elastic, while complete pieces of elastic nonwoven material may be used for the waist elastic. It is also conceivable for the elastic devices 11–14 to comprise parts of mutually different materials. For instance, as shown in FIG. 7, the parallel parts of the threads 11, 12 can be replaced with a centrally extending band 19 while the diverging parts are comprised of elastic threads. Thus, there are two elastic devices defined by two elastic threads extending from the front-part to the region V, and there is one elastic device extending from the region V rearward through the back-part of the panty.

Figure 6:
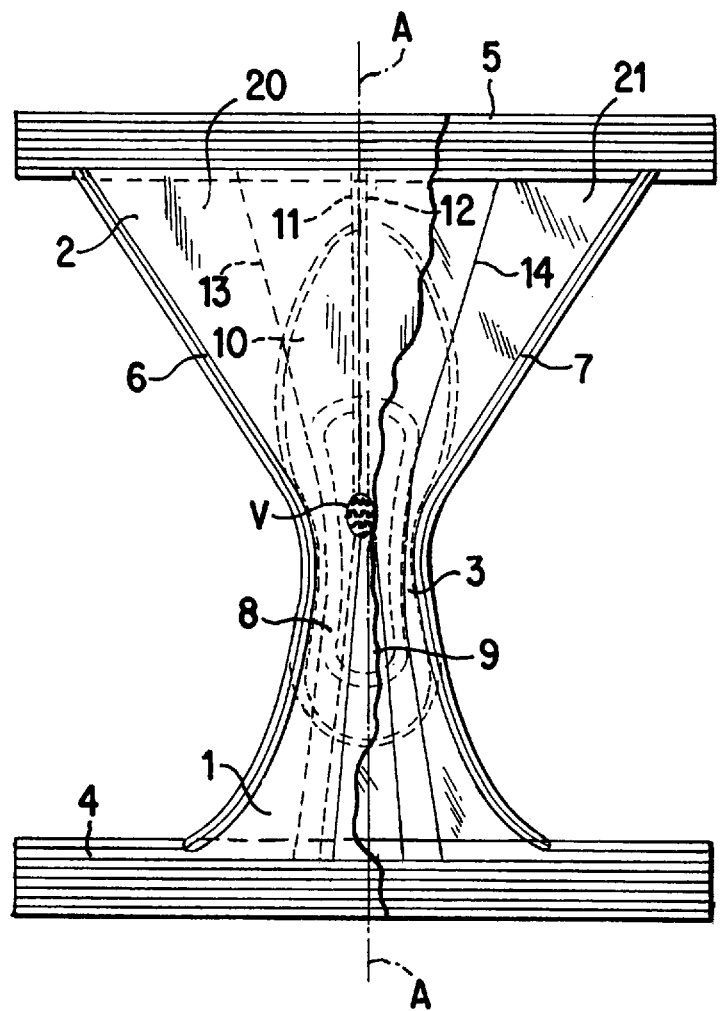
FIG. 6 is a partially broken away view of the first embodiment of the inventive sanitary panty shown in FIG. 1.

Referring also to FIG. 6, the panty illustrated in FIG. 1 is preferably comprised of two sheets 20, 21 which are mutually joined in some appropriate manner, for instance by gluing or ultrasonic welding, and the elastic devices are mounted between these sheets and fastened thereto, for instance glued or welded with ultrasonic welds or heat welds. The elastic may also be sewn in the panty.

As before mentioned, the absorbent body 8 illustrated in FIG. 1 is comprised of a primary and a secondary absorbent body 9 and 10, respectively. The primary absorbent body 9 is constructed in the same manner as a conventional absorbent body or pad of a sanitary napkin and will have an absorbency sufficient to handle fluid discharged by the wearer over the intended use time-period, for instance a full night. For instance, the absorbent body may be comprised of one or more layers of compressed cellulose fluff which may or may not contain superabsorbent material. The absorbent body 9 is advantageously comprised of one or more layers of roll material, i.e. absorbent material which has earlier been compressed and treated so that the materials can be stored in the form of rolls. Such absorbent bodies may be very thin and pliable while still having sufficiently high absorbency for use as a night napkin. The secondary absorbent body 10 has much larger extensions than the primary absorbent body and extends rearwardly over a larger part of the back-part of the panty. The primary purpose of the secondary absorbent body is to enhance leakage safety and shall therefore have a given absorbency. To this end, the secondary absorbent body may be comprised of tissue, nonwoven or other roll material. The secondary absorbent body 10 will also preferably contain means for preventing liquid from spreading over the surface of said body. Such fluid-spreading barriers may be obtained, for instance, by folding, pleating or crêping the material sheet or layer of said body, or by providing barrier-type welds. It is also conceivable to use a nonwoven material which includes fibres of so-called superabsorbent material which, when absorbing fluid, bind the absorbed fluid chemically. However, the secondary absorbent body will, in general, be equally as pliable and supple as the panty material, so that the panty can be worn comfortably. The secondary absorbent body must therefore be made very thin and will subsequently have highly limited absorbency.

The combined absorbent body 8, comprising the primary and the secondary absorbent bodies, is enclosed conventionally between a fluid-permeable casing sheet and a fluid-impermeable but advantageously air-permeable casing sheet which lies against the panty in use.

As will be seen from FIG. 1, the side-contours of the secondary absorbent body follow the side-contours of the panty within the region of the narrowest part of the crotch-part. This is highly advantageous when the combined absorbent body 8 is a removable type body, since its configuration clearly indicates where the absorbent body 8 shall be placed in the panty. This eliminates to a large extent the risk of a user placing the absorbent body wrongly in the panty.

As will be understood, the described panty can be used together with absorbent bodies other than the absorbent body described with reference to the exemplifying embodiment, such as an absorbent body which lacks a secondary absorbent body of the aforedescribed kind. The absorbent body may also have a shape different to that shown in FIG. 1, for instance a rectangular shape.

Figure 5:
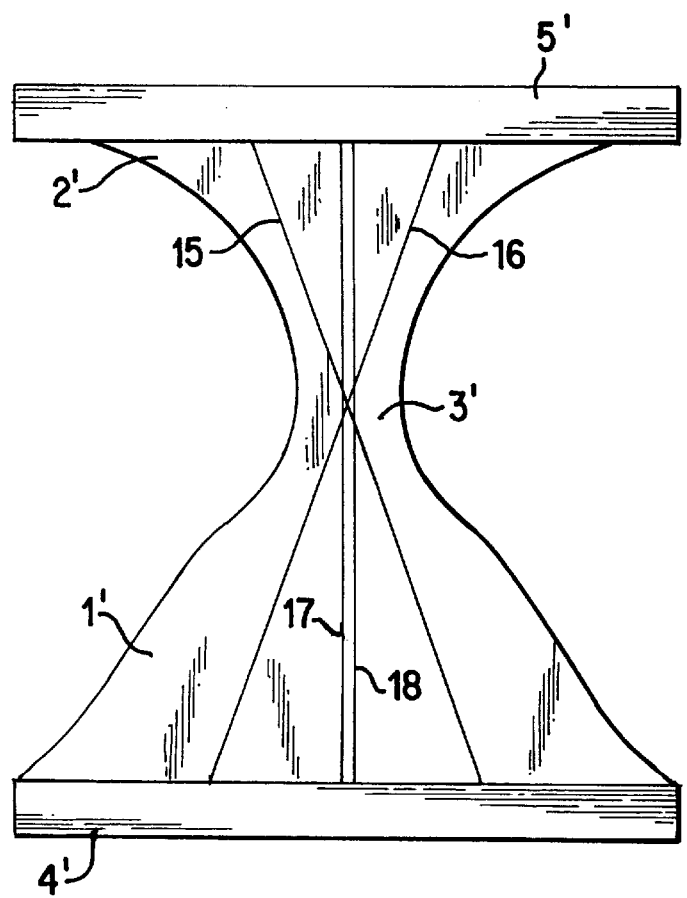
FIG. 5 is a view similar to FIG. 1 illustrating a second embodiment of an inventive sanitary panty.

FIG. 5 shows a second embodiment of an inventive sanitary panty. Those panty components of the FIG. 5 embodiment which find correspondence in the panty illustrated in FIG. 1 have been identified by the same reference signs to which a prime has been added.

In the case of the panty illustrated in FIG. 5, two elastic threads 15, 16 extend obliquely and symmetrically relative to a central long line through the front-part, the crotch-part and the back-part of the panty, from the front-edge of the front-part 1' to the rear-edge of the back-part 2'. The threads 15, 16 cross one another at a point located in the crotch region of a user wearing the panty. Similar to the panty illustrated in FIG. 1, the panty includes two threads which diverge away from one another in a forward direction from the crotch region. These parts of the threads 15, 16 act in a manner analogous with the aforedescribed corresponding thread-parts of the FIG. 1 embodiment when wearing the panty with an inserted absorbent body.

The threads 15, 16 can be supplemented with threads 17, 18 which extend parallel with one another close to the aforesaid central line, so as to cause a coacting absorbent body rearwardly of the crotch region to be pressed in against the wearer's body between the buttocks thereof.

It will be understood that the aforedescribed embodiments can be modified in several ways within the scope of the invention. For instance, the panty may be constructed from one single material sheet. The panty may also include transverse elastics within the region of the primary absorbent body, particularly when the absorbent body is integral with the panty, so as to deform an inserted absorbent body in the manner desired. In the case of removable absorbent bodies, the absorbent bodies may also be fastened to the panty within the region of such transverse elastic. Further elastic threads may also be mounted between the laterally outermost threads 13 and 14, these threads also extending in a convergent-divergent pattern in relation to one another. An absorbent layer corresponding to the secondary absorbent body in the panty of FIG. 1 may also be formed integrally with the panty. In this case, an absorbent body coacting with a panty of this nature need only be enclosed in a fluid-permeable casing layer. The invention is therefore limited solely by the content of the following claims.

I claim:
1. A sanitary panty, comprising:
   a back-part having lateral sides,
   a front-part having lateral sides, the lateral sides of the back-part being joined to the lateral sides of the front-part so as to form a waist and define leg openings,
   an intermediate crotch-part, and
   elastic means which extend between the front-part and the back-part of the panty for pressing an absorbent body attached to the panty into abutment with a wearer's body,
   said elastic pressing means includes two elastic devices which extend from a laterally centrally located region in the crotch-part of the panty to a front-edge of the front-part while diverging relative to one another and extending generally symmetrically in relation to a central line which extends through the back-part, the crotch-part and the front-part of the panty.

2. A sanitary panty according to claim 1, wherein at least one of the two elastic devices extends from the region in the crotch-part to a rear edge of the back-part parallel and adjacent to the central line.

3. A sanitary panty according to claim 1, wherein the two elastic devices extend from the region in the crotch-part to a rear-edge of the back-part while diverging relative to one another and extending symmetrically in relation to the central line.

4. A sanitary panty according to claim 1, further comprising additional elastic devices that extend divergently in relation to one another and symmetrically in relation to the central line, from the region in the crotch-part to a rear-edge of the back-part and to the front-edge of the front-part.

5. A sanitary panty according to claim 4, wherein, at least within the region in the crotch-part, the additional elastic devices lie outermost in relation to the central line and extend along side-edges of the absorbent body attached to the panty.

6. A sanitary panty according to claim 1, wherein the elastic pressing means are comprised of one of elastic threads, bands and ribbons.

7. A sanitary panty according to claim 1, wherein the panty is comprised of two sheets, and the elastic pressing means are mounted between said two sheets.

8. A sanitary panty according to claim 7, wherein the two sheets are joined to one another and to the elastic pressing means.

9. A sanitary panty according to claim 8, wherein the two sheets are adjoined to one another and to the elastic pressing means by gluing.

10. A sanitary panty according to claim 8, wherein the two sheets are joined to one another and to the elastic pressing means by ultrasonic welding.

11. A sanitary panty according to claim 1, wherein the absorbent body is permanently mounted to the panty.

12. A sanitary panty according to claim 1, wherein the absorbent body is removably attached to the panty.

13. A sanitary panty according to claim 1, wherein the two elastic devices extend along the central line from the region in the crotch-part to a rear edge of the back-part.

14. A sanitary panty according to claim 13, wherein the two elastic devices extend close together.

15. A sanitary panty according to claim 1, wherein the two elastic devices extend along the central line from a rear edge of the back-part to the region in the crotch-part for pressing a portion of the absorbent body between buttocks of the wearer.

16. A sanitary panty according to claim 15, wherein the two elastic devices extend close together.

17. A sanitary panty according to claim 1, further comprising an elastic device overlying the central line from the region in the crotch-part to a rear edge of the back-part.

18. An incontinence guard panty comprising:

a back-part having lateral sides, a front-part having lateral sides, the lateral sides of the back-part being joined to the lateral sides of the front-part so as to form a waist and define leg openings, an intermediate crotch-part, and elastic means which extend between the front-part and the back-part of the incontinence guard panty for pressing an absorbent body attached to the incontinence guard panty into abutment with a wearer's body, said elastic pressing means includes two elastic devices which extend from a laterally centrally located region in the crotch-part of the incontinence guard panty to a front-edge of the incontinence guard panty while diverging relative to one another and extending generally symmetrically in relation to a central line which extends through the back-part, the crotch-part and the front-part of the incontinence guard.

19. An incontinence guard panty according to claim 18, wherein the absorbent body is permanently mounted to the incontinence guard.

20. An incontinence guard panty according to claim 18, wherein the absorbent body is removably attached to the incontinence guard.

21. An incontinence guard panty according to claim 18, wherein at least one of the two elastic devices extends from the region in the crotch-part to a rear edge of the back-part parallel and adjacent to the central line.

22. An incontinence guard panty according to claim 18, wherein the two elastic devices extend along the central line from the region in the crotch-part to a rear edge of the back-part.

23. An incontinence guard panty according to claim 22, wherein the two elastic devices extend close together and parallel with the central line.

24. An incontinence guard panty according to claim 18, wherein the two elastic devices extend along the central line from a rear edge of the back-part to the region in the crotch-part for pressing a portion of the absorbent body between buttocks of the wearer.

25. An incontinence guard panty according to claim 24, wherein the two elastic devices extend close together and parallel with the central line.

26. A sanitary panty comprising:

a back-part having lateral sides, a front-part having lateral sides, an intermediate crotch-part having lateral sides, the lateral sides of the front and back-parts being joined together to form leg openings and a waist opening, an absorbent body attached to the panty in the crotch-part on an inside thereof which faces a wearer's body when the panty is used, and two elastic devices for pressing the absorbent body attached to the panty into abutment with the wearer's body, the two elastic devices extending from the crotch-part of the panty to the back-part of the panty adjacent to a central line which extends through the back-part, the crotch-part and the front part of the panty, wherein, at the crotch-part, the two elastic devices are closer to the central line than to the crotch-part lateral sides, and the two elastic devices extend from the crotch-part to a front-edge of the front-part of the panty while diverging relative to one another.

27. A sanitary panty according to claim 26, wherein said two elastic devices extend from a laterally centrally located region of the crotch-part.

28. A sanitary panty according to claim 26, wherein said two elastic devices extend parallel to the central line from the crotch-part to the back-part.

* * * * *